United States Patent [19]

Matsushita

[11] Patent Number: 4,529,555
[45] Date of Patent: Jul. 16, 1985

[54] SURFACE MODIFIER FOR POWDERY OR GRANULAR SUBSTANCE HAVING HYDROPHILIC SURFACE COMPRISING AN ALUMINUM CHELATE COMPOUND

[75] Inventor: Noritaka Matsushita, Takefu, Japan

[73] Assignees: Kawaken Fine Chemicals Co., Ltd.; Ajinomoto Co., Inc., both of Tokyo, Japan

[21] Appl. No.: 424,452

[22] Filed: Sep. 27, 1982

[51] Int. Cl.$^3$ .................................................. C07F 5/06
[52] U.S. Cl. ....................................... 556/174; 556/175
[58] Field of Search ............ 260/448 B, 429 J, 448 AD

[56] References Cited

U.S. PATENT DOCUMENTS

| | | | |
|---|---|---|---|
| 2,839,421 | 6/1958 | Albisetti | 260/448 AD X |
| 2,844,551 | 7/1958 | Arthner et al. | 260/448 B |
| 2,871,135 | 1/1959 | Weiss | 260/448 AD X |
| 3,197,436 | 7/1965 | Block et al. | 260/448 B |
| 3,244,646 | 4/1966 | Naro et al. | 260/448 AD |
| 4,083,860 | 4/1978 | Ruf | 260/448 AD |
| 4,132,724 | 1/1979 | Turner | 260/448 AD |

*Primary Examiner*—Helen M. S. Sneed
*Attorney, Agent, or Firm*—McAulay, Fields, Fisher, Goldstein & Nissen

[57] ABSTRACT

A surface modifier for a powdery or granular substance having a hydrophilic surface is provided. The surface modifier comprises an aluminum chelate compound of the formula (I):

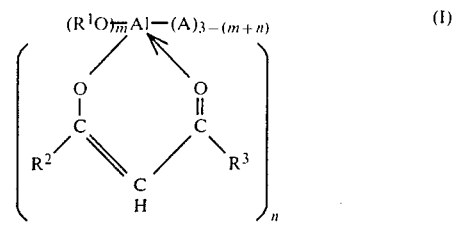

wherein $R^1$ is selected from hydrogen and C1-6 alkyl, $R^2$ is selected from methyl and phenyl, $R^3$ is selected from $R^4-$, $R^5O-$ and $R^6NH-$, A is selected from $R^7O-$, $R^8COO-$, $R^9SO_3-$, $R^{10}OSO_3-$,

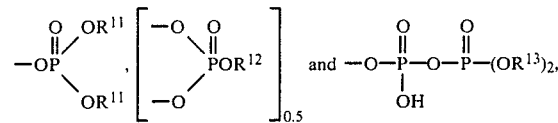

$R^4$, $R^5$, $R^6$, $R^7$, $R^8$, $R^9$, $R^{10}$, $R^{11}$, $R^{12}$ and $R^{13}$ are C1-22 alkyl or C3-22 alkenyl, aryl, aralkyl or alkylarly, $R^3$ may be the same as or different from $R^7$, $R^8$, $R^9$, $R^{10}$, $R^{11}$, $R^{12}$ and $R^{13}$, with the proviso that at least one of $R^3$, $R^7$, $R^8$, $R^9$, $R^{10}$, $R^{11}$, $R^{12}$, and $R^{13}$ is a substituent having at least 8 carbon atoms of a polymerizable alkenyl group, and m=0.5 to 2.7, n=0.3 to 2.5 and m+n=0.8 to 3.

2 Claims, No Drawings

SURFACE MODIFIER FOR POWDERY OR GRANULAR SUBSTANCE HAVING HYDROPHILIC SURFACE COMPRISING AN ALUMINUM CHELATE COMPOUND

BACKGROUND OF THE INVENTION (1) Field of the Invention

This invention relates to a surface modifier for a powdery or granular substance having a hydrophilic surface, such as a filler or pigment for polymeric compound. More particularly, it relates to a surface modifier for treating a powdery or granular substance having a hydrophilic surface with an aluminum chelate compound to modify this hydrophilic surface and improve the dispersibility of the powdery or granular substance in an organic medium.

(2) Description of the Prior Art

Ordinarily, a filler or pigment for a polymeric compound (hereinafter referred to as "filler or the like" for brevity) has hydrophilic functional groups and adsorbed water on the surface thereof whereby the surface of the filler or the like is kept hydrophilic. Accordingly, the filler or the like is poor in the oleophilic characteristic and it does not show good dispersibility or miscibility to organic media such as paint vehicles, printing ink vehicles and polymeric compounds. Therefore, if the filler or the like is used as it is, the gloss or opacitying power of a paint or printing ink is degraded or the strength of a composite plastic material is reduced. As means for eliminating this defect, many proposals have been made which include, for example, a method in which a surface active agent or metal soap is added together with the filler or the like and a method in which the filler or the like is treated with an organic silane type coupling agent. Furthermore, they include a method in which aluminum triacylate or its derivatives are incorporated in an organic medium to improve the dispersibility of the filler or the like in said organic medium (see U.S. Pat. No. 3,294,686), a method in which the filler or the like is treated with a titanium compound containing a partially hydrolyzed group and a method in which the filler or the like is treated with an aluminum alcoholate of a lower or higher alcohol or a partially acylated product thereof (see U.S. Pat. No. 3,905,936). These known methods are effective for improving the dispersibility of the filler or the like to some extent, but their modifying effect is not satisfactory, the production of the modifiers is not easy, they readily solidify or a large amount of a solvent is necessary because the solubility is poor.

SUMMARY OF THE INVENTION

It is therefore a primary object of the present invention to provide a surface modifier for a powdery or granular substance having a hydrophilic surface, which exhibits an improved surface-modifying effect without any of the foregoing defects.

In accordance with the present invention, there is provided a surface modifier for a powdery or granular substance having a hydrophilic surface, which comprises at least one aluminum chelate compound represented by the following general formula (1):

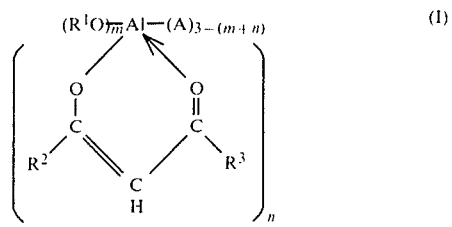

wherein $R^1$ is at least one member selected from a hydrogen atom and an alkyl group having 1 to 6 carbon atoms, $R^2$ is at least one member selected from methyl and phenyl groups, $R^3$ is at least one member selected from $R^4-$, $R^5O-$ and $R^6NH-$, A is at least one member selected from $R^7O-$, $R^8COO-$, $R^9SO_3-$, $R^{10}OSO_3-$,

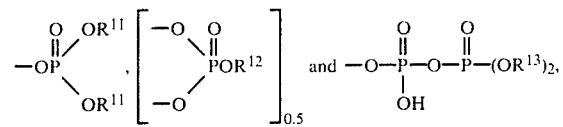

$R^4$, $R^5$, $R^6$, $R^7$, $R^8$, $R^9$, $R^{10}$, $R^{11}$, $R^{12}$ and $R^{13}$ stand for an alkyl group having 1 to 22 carbon atoms or an alkenyl, aryl, aralkyl or alkylaryl group having 3 to 22 carbon atoms, $R^3$ may be the same as or different from $R^7$, $R^8$, $R^9$, $R^{10}$, $R^{11}$, $R^{12}$ and $R^{13}$, with the proviso that at least one of $R^3$, $R^7$, $R^8$, $R^9$, $R^{10}$, $R^{11}$, $R^{12}$ and $R^{13}$ is a substituent having at least 8 carbon atoms or a polymerizable alkenyl group, and m and n are mean values per molecule which satisfy the requirements of m=0.5 to 2.7, n=0.3 to 2.5 and m+n=0.8 to 3.

DESCRIPTION OF THE PREFERRED EMBODIMENTS

Some of the aluminum chelate compounds used in the present invention are novel.

The aluminum chelate compounds used in the present invention will now be described in detail.

In the general formula (I), the group $R^1O-$ should be reactive with the hydrophilic surface of the filler or the like on which a hydrophilic functional group such as a hydroxyl group or adsorbed water is present. A high reactivity is desirable for this group. A group $R^1O-$ in which $R^1$ has a long chain is not preferred because the reactivity is low. Thus, $R^1$ is selected from a hydrogen atom and an alkyl group having 1 to 6 carbon atoms. It is preferred that $R^1$ be a hydrogen atom or an isopropyl, sec-butyl or isobutyl group. Hydrocarbon substituents $R^4$ through $R^{13}$ in A and $R^3$ in the general formula (I) are as defined above, and preferred examples of these substituents are methyl, ethyl, butyl, capryl, lauryl, myristyl, palmityl, cetyl, stearyl, oleyl, dodecylphenyl, benzyl, nonylphenyl, isopropenyl and allyl groups. These groups $R^4$ through $R^{13}$ impart an oleophilic characteristic to the surface of the filler or the like. Accordingly, at least one of the groups $R^4$ through $R^{13}$ should contain a substituent having at least 8 carbon atoms or a polymerizable alkenyl group. These groups $R^4$ through $R^{13}$ may be substituted by a functional group such as an amino group or a hydroxyl group.

In the general formula (I), m, n and 3−(m+n), which are values indicating the ratios of the respective substituents to the aluminum atom, are determined while the balance between the intensity of the reaction of the aluminum compound of the present invention with the hydrophilic surface of the filler or the like and the oleophilic characteristic to be imparted is taken into account.

More specifically, in the aluminum compound of the present invention, m as the mean value per molecule is 0.5 to 2.7, preferably 1 to 2, and n as the mean value per molecule is 0.3 to 2.5, preferably 0.5 to 2, and m+2 is 0.8 to 3. If the mean value of m is smaller than 0.5, the reactivity of the aluminum compound with the hydrophilic surface becomes poor because the proportion of the group $R^1O$ is too small. If the mean value of m exceeds 2.7, the reactivity is undesirably too high.

The aluminum chelate compounds used in the present invention include, for example, the following compounds.

(1) Mono-(oleyl 3-oxobutanoato-$O^1,O^3$)-bis-(2-propanolato)-aluminum, (2) Bis-(oleyl 3-oxobutanoato-$O^1,O^3$)-mono-(2-propanolato)-aluminum, (3) Mono-(oleyl 3-oxobutanoato-$O^1,O^3$)-mono-acrylato-mono-(2-propanolate)-aluminum, (4) Mono-(ethyl 3-oxobutanoato-$O^1,O^3$)-mono-(oleato)-mono-(2-propanolato)-aluminum, (5) Mono-(oleyl 3-oxobutanoato-$O^1,O^3$)-mono-(ethyl 3-oxobutanoato-$O^1,O^3$)-mono-(2-propanolato)-aluminum, (6) Mono-(isostearyl 3-oxobutanoato-$O^1,O^3$)-mono-(rhodinato)-mono-(2-propanolato)-aluminum, (7) Mono-(lauryl 3-oxobutanoato-$O^1,O^3$)-mono-(N-lauroyl β-alanato)-mono-(2-propanolato)-aluminum, (8) (Dioctyl phosphato-O)-(9-octadecenyl-3-oxobutanoato-$O^1,O^3$)-(2-propanolato)-aluminum, (9) (Dibutyl phosphato-O)$_\frac{1}{2}$-(butyl phosphato-O,O)$_\frac{1}{4}$-(9-octadecenyl 3-oxobutanoato-$O^1,O^3$)-(2-propanolato)-aluminum,

(10) (Dioctyl phosphato-O)$_\frac{1}{2}$-(octyl phosphato-O,O)$_\frac{1}{4}$-(9-octadecenyl-3-oxobutanoato-$O^1,O^3$)-(2-propanolato)-aluminum,

(11) (Dioctyl phosphato-O)$_\frac{1}{2}$-(octyl phosphato-O,O)$_\frac{1}{4}$-hydroxy-(9-octadecenyl 3-oxobutanoato-$O^1$, $O^3$)-aluminum,

(12) (Dioctyl phosphato-O)$_\frac{1}{2}$-(octyl phosphato-O,O)$_\frac{1}{4}$-(ethyl 3-oxobutanoato-$O^1,O^3$)-(2-propanolato)-aluminum,

(13) (Dioctyl phosphato-O)$_\frac{3}{4}$-(octyl phosphato-O,O)$_\frac{3}{8}$-(9-octadecenyl 3-oxobutanamido-$O^1,O^3$)-(2-propanolato)$_\frac{1}{2}$-aluminum,

(14) (2,2-Dioctyl pyrophosphato-O)-(9-octadecenyl 3-oxobutanoato-$O^1,O^3$)-(2-propanolato)-aluminum,

(15) (4-Dodecylphenyl sulfonato-O)-(9-octadecenyl 3-oxobutanoato-$O^1,O^3$)-(2-propanolato)-aluminum,

(16) (4-Dodecylphenyl sulfonato-O)-hydroxy-(9-octadecenyl 3-oxobutanoato-$O^1,O^3$)-aluminum,

(17) (Dodecyl sulfato-O)-(9-octadecenyl 3-oxobutanoato-$O^1,O^3$)-(2-propanolato)-aluminum,

(18) (4-Dodecylphenyl sulfonato-O)-(9-octadecenyl 3-oxo-3-phenylpropionato-$O^1,O^3$)-(2-propanolato)-aluminum,

(19) (Methyl sulfonato-O)-(9-octadecenyl 3-oxobutanoato-$O^1,O^3$)-(2-propanolato)-aluminum,

(20) (4-Dodecylphenyl sulfonato-O)-(2,4-pentanedionato-O,$O^1$)-(2-propanolato)-aluminum, and

(21) (4-Dodecylphenyl sulfonato-O)-(octyl 3-oxobutanamido-$O^1,O^3$)-(2-propanolato)-aluminum.

For better illustration, the substituents of the foregoing compounds (1) through (21) are shown below.

| | $R_1$ | $R_2$ | $R_3$ | A | m | n |
|---|---|---|---|---|---|---|
| (1) | i-$C_3H_7$— | $CH_3$— | —$OC_{18}H_{35}$ | Not present | 2 | 1 |
| (2) | i-$C_3H_7$— | $CH_3$— | —$OC_{18}H_{35}$ | Not present | 1 | 2 |
| (3) | i-$C_3H_7$— | $CH_3$— | —$OC_{18}H_{35}$ | —OCOCH=$CH_2$ | 1 | 1 |
| (4) | i-$C_3H_7$— | $CH_3$— | —$OC_2H_5$ | —OCO$C_{17}H_{33}$ | 1 | 1 |
| (5) | i-$C_3H_7$— | $CH_3$— | —$OC_{18}H_{35}$ | —OCO$CH_2$CO$CH_3$ | 1 | 1 |
| (6) | i-$C_3H_7$— | $CH_3$— | —$OC_{18}H_{37}$ | 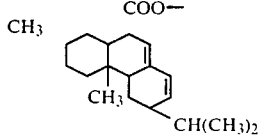 | 1 | 1 |
| (7) | i-$C_3H_7$— | $CH_3$— | —$OC_{12}H_{25}$ | 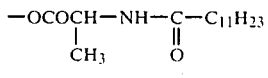 | 1 | 1 |
| (8) | i-$C_3H_7$— | $CH_3$— | —$OC_{18}H_{35}$ | 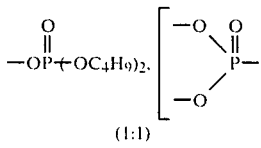 | 1 | 1 |
| (9) | i-$C_3H_7$— | $CH_3$— | —$OC_{18}H_{35}$ | 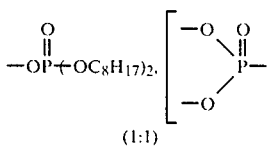 | 1 | 1 |
| (10) | i-$C_3H_7$— | $CH_3$— | —$OC_{18}H_{35}$ |  | 1 | 1 |

-continued

| | R₁ | R₂ | R₃ | A | m | n |
|---|---|---|---|---|---|---|
| (11) | H | $CH_3-$ | $-OC_{18}H_{35}$ | " | 1 | 1 |
| (12) | $i\text{-}C_3H_7-$ | $CH_3-$ | $-OC_2H_5$ | " | 1 | 1 |
| (13) | $i\text{-}C_3H_7-$ | $CH_3-$ | $-NHC_{18}H_{35}$ | " | 0.5 | 1 |
| (14) | $i\text{-}C_3H_7-$ | $CH_3-$ | $-OC_{18}H_{35}$ | $-O\overset{O}{\underset{OH}{\overset{\|}{P}}}-O-\overset{O}{\overset{\|}{P}}(O-C_8H_{17})_2$ | 1 | 1 |
| (15) | $i\text{-}C_3H_7-$ | $CH_3-$ | $-O-C_{18}H_{35}$ | $-OSO_2-\langle\bigcirc\rangle-C_{12}H_{25}$ | 1 | 1 |
| (16) | H | $CH_3-$ | $-O-C_{18}H_{35}$ | $-OSO_2-\langle\bigcirc\rangle-C_{12}H_{25}$ | 1 | 1 |
| (17) | $i\text{-}C_3H_7-$ | $CH_3-$ | $-OC_{18}H_{35}$ | $-OSO_2-OC_{12}H_{25}$ | 1 | 1 |
| (18) | $i\text{-}C_3H_7-$ | $\langle\bigcirc\rangle-$ | $-OC_{18}H_{35}$ | $-OSO_2-\langle\bigcirc\rangle-C_{12}H_{25}$ | 1 | 1 |
| (19) | $i\text{-}C_3H_7-$ | $CH_3-$ | $-OC_{18}H_{35}$ | $-OSO_2-CH_3$ | 1 | 1 |
| (20) | $i\text{-}C_3H_7-$ | $CH_3-$ | $-CH_3$ | $-OSO_2-\langle\bigcirc\rangle-C_{12}H_{25}$ | 1 | 1 |
| (21) | $i\text{-}C_3H_7-$ | $CH_3-$ | $-NHC_{18}H_{37}$ | $-OSO_2-\langle\bigcirc\rangle-C_{12}H_{25}$ | 1 | 1 |

These aluminum compounds can be prepared, for example, according to the following methods.

(1) An aluminum alkoxide such as aluminum isopropoxide or aluminum butoxide is reacted with a β-keto ester. This reaction is expressed by the following reaction formula:

$$Al(OR^1)_3 + R^2COCH_2COOR^3 \longrightarrow$$

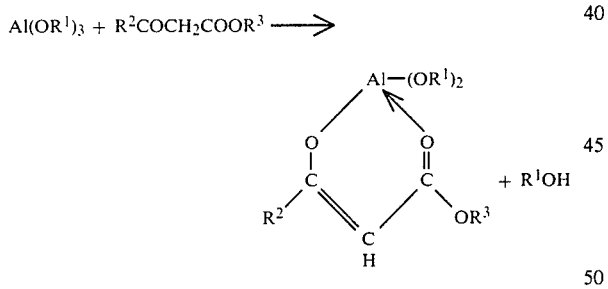

$+ R^1OH$ (2) An aluminum alkoxide is reacted with a β-keto ester and an acidic phosphoric acid ester. This reaction is represented by the following reaction formula:

$$Al(OR^1)_3 + R^2COCH_2COOR^3 + (R^4O)_2\overset{O}{\overset{\|}{P}}-OH \longrightarrow$$

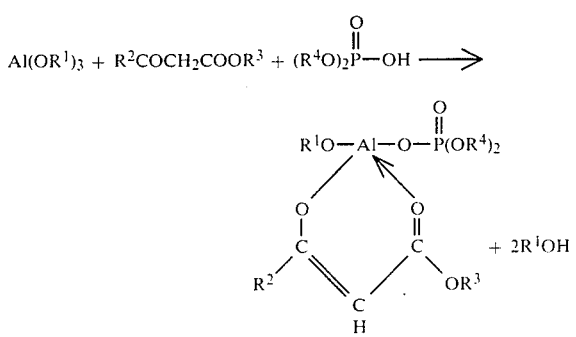

$+ 2R^1OH$ (3) An aluminum alkoxide is reacted with sulfonic acid and a β-keto ester. This reaction is represented by the following reaction formula:

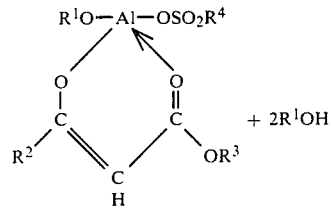

$+ 2R^1OH$

The surface modifier of the present invention, which comprises the above-mentioned aluminum compound, is used for modifying the hydrophilic surface of the filler or the like. The amount of the aluminum compound used for the modification is from 0.1 to 20% by weight, preferably 0.5 to 3% by weight, based on the filler or the like. As the method for treating the filler or the like with the aluminum compound of the present invention, there may be adopted a method in which the aluminum compound is incorporated, as it is or after dilution with an appropriate diluent, with the filler or the like in a mixer, a method in which the aluminum compound and the filler or the like are incorporated in an organic solvent and thereafter the solvent is removed therefrom, and a method in which the aluminum compound is incorporated, as it is, in a mixture of an organic solvent and the filler or the like.

As the filler or the like to be modified with the aluminum chelate compound of the present invention, there can be mentioned inorganic and organic fillers and pigments, such as calcium carbonate, kaolin, mica, aluminum hydroxide, titanium dioxide, silica, zinc yellow, red lead, red iron oxide, zinc flower, talc, carbon black, barium sulfate, magnesium carbonate, asbestos, glass fiber, Phthalocyanine Blue, Quinacridone Yellow and Lake Red C. Of course, substances that can be modified by the aluminum chelate compound of the present invention are not limited to those exemplified above, and various substances having a hydrophilic surface can be modified by the aluminum chelate compound of the present invention. As pointed out hereinbefore, by the substance having a hydrophilic surface is meant a substance having on the surface thereof a hydrophilic functional group such as a hydroxyl group or water of crystallization or adsorbed water.

The filler or the like having the surface modified by the aluminum compound of the present invention can be applied to various organic media, which include, for example, vehicles for paints and printing inks, composed of drying oils such as linseed oil, tung oil and soybean oil, synthetic drying oils such as dehydrated castor oil, maleic oil, styrenated oil and vinyl toluene-modified oil, natural and modified resins such as rosin, hardened rosin, polymerized rosin, rosin ester, maleic acid resin, shellac and casein, synthetic resins such as phenolic resin, xylene resin, modified alkyd resin, polyamide resin and coumarone-indene resin, rubber derivative such as chlorinated rubber and cyclized rubber, or cellulose derivatives such as nitro cellulose and ethyl cellulose; solvents and diluents such as hexane, toluene, xylene and cellosolve; and molding polymeric compounds such as polyethylene resin, polypropylene resin, polystyrene resin, polyvinyl chloride resin, polyester resin, polycarbonate resin, silicone resin, acrylic resin, fluorine resin, epoxy resin, ABS resin and BS resin.

The filler or the like having the surface modified with the aluminum chelate compound of the present invention can be applied, in combination with an organic medium as described above, to various articles such as printing inks, paints, polyvinyl chloride plastic tiles, flame-retardant plastics containing a large amount of aluminum hydroxide or calcium carbonate, and pollution-free plastics comprising a polyolefin resin and calcium carbonate.

The filler or the like modified by the aluminum chelate compound of the present invention has various advantages. For example, when the modified filler or the like is applied to a paint or printing ink, (1) the sharpness is improved, (2) the gloss or hiding power is increased and (3) the mixing time is shortened at the ink- or paint-manufacturing step. When the modified filler or the like is used for plastics, (1) the amount of the filler or the like in corporated with the plastics is increased, (2) the flowability is improved, (3) physical properties of products are improved, and (4) the mixing time is shortened.

It is believed that these excellent effects are due to the fact that since the aluminum chelate compound of the present invention contains not only a group reactive with a hydroxyl group or adsorbed water on the surface of the filler or the like but also an oleophilic group bonded to a stable chelate, sulfonic acid or phosphoric acid ester group, the aluminum chelate compound has an improved compatibility with both the organic medium and the filler or the like.

The present invention will now be described in detail with reference to the following Examples that by no means limit the scope of the invention. Incidentally, the compound numbers in the Examples correspond to the numbers of the compounds exemplified hereinbefore.

REFERENCE EXAMPLE 1

Preparation of Compound (1)

A four-neck flask equipped with a stirrer, a thermometer, a dropping funnel and a cooler was charged with 204 g (1 mole) of aluminum isopropylate, and 370 g (1 mole) of oleyl acetoacetate was dropped from the dropping funnel with stirring over a period of 30 minutes while the liquid temperature was maintained at 50° to 60° C. After completion of the dropwise addition, the temperature was gradually elevated to 130° C., and at this temperature, reaction was carried out with stirring while distilling isopropanol formed by the reaction. After completion of distillation of isopropanol, the reaction was further conducted for 15 minutes to obtain 415 g of the compound (1) in the form of an oily liquid.

Aluminum Content: 5.44% (found), 5.45% (calculated).

REFERENCE EXAMPLE 2

Preparation of Compound (2)

A four-neck flask equipped with a stirrer, a thermometer, a dropping funnel and a cooler was charged with 495 g (1 mole) of mono-(oleyl 3-oxobutanoate-$O^1,O^3$)-bis-(2-propanolate)-aluminum, and 351 g (1 mole) of oleyl acetoacetate was dropped from the dropping funnel at room temperature with stirring over a period of 30 minutes. After completion of the dropwise addition, the temperature was elevated to 130° C. by heating, and reaction was carried out with stirring while distilling isopropanol formed by the reaction. After completion of distillation of isopropanol, the reaction was further conducted under reduced pressure for 15 minutes to obtain 770 g of the compound (2) in the form of an oily liquid.

Aluminum Content: 3.49% (found), 3.43% (calculated).

REFERENCE EXAMPLE 3

Preparation of Compound (8)

A 2-liter four-neck flask equipped with a stirrer, a thermometer, a dropping funnel and a cooler was charged with 204 g (1 mole) of aluminum isopropoxide and 400 ml of toluene, and 351 g (1 mole) of oleyl acetoacetate was dropped from the dropping funnel at room temperature with stirring over a period of 30 minutes. Then, a solution of 322 g (1 mole) of dioctyl phosphate in 300 ml of toluene was similarly added dropwise. After completion of the dropwise addition, the mixture was heated and refluxed for 30 minutes. Toluene and isopropyl alcohol formed by reaction were distilled off under reduced pressure to obtain 757 g of the compound (8) in the form of an oily liquid.

Aluminum Content: 3.55% (found), 3.56% (calculated).

REFERENCE EXAMPLE 4

Preparation of Compound (15)

A 2-liter four-neck flask equipped with a stirrer, a thermometer, a dropping funnel and a cooler was charged with 204 g (1 mole) of aluminum isoproxide and 400 ml of toluene, and at room temperature with stirring, 352 g (1 mole) of oleyl acetoacetate and then 327 g (1 mole) of dodecyl benzenesulfonate were added dropwise from the dropping funnel. After completion of the dropwise addition, the mixture was heated and refluxed for 30 minutes, and toluene and formed isopropyl alcohol were distilled off under reduced pressure to obtain 762 g of the compound (15) in the form of an oily liquid.

Aluminum Content: 3.64% (found), 3.54% (calculated).

Characteristic Infrared Absorptions: 1605 cm$^{-1}$ (C=O of chelate), 1125 cm$^{-1}$ and 1040 cm$^{-1}$ (SO$_2$).

REFERENCE EXAMPLE 5

Preparation of Compound (16)

In the same manner as described in Reference Example 4 oleyl acetoacetate and dodecyl benzenesulfonate were added dropwise to the toluene solution of aluminum isopropoxide. Then, a solution of 18 g (1 mole) of water in 100 ml of isopropyl alcohol was added dropwise to the mixture. After completion of the dropwise addition, the mixture was heated and refluxed for 30 minutes, and toluene and formed isopropyl alcohol were distilled off under reduced pressure to obtain 721 g of the compound (16) in the form of an oily liquid.

Aluminum Content: 3.85% (found), 3.75% (calculated).

Characteristic Infrared Absorptions: 3400 cm$^{-1}$ (OH), 1605 cm$^{-1}$ (C=O of chelate), 1125 cm$^{-1}$ and 1040 cm$^{-1}$ (SO$_2$).

REFERENCE EXAMPLE 6

Preparation of Compound (17)

In the same manner as described in Reference Example 4, reaction was carried out by using 204 g (1 mole) of aluminum isopropoxide, 352 g (1 mole) of oleyl acetoacetate and 266 g (1 mole) of dodecyl sulfate, whereby 702 g of the compound (17) was obtained in the form of an oily liquid.

Aluminum Content: 3.77% (found), 3.85% (calculated).

Characteristic Infrared Absorptions: 1605 cm$^{-1}$ (C=O of chelate), 1060 cm$^{-1}$ (O—SO$_2$—O).

EXAMPLE 1

The effect of improving the sharpness of a printing ink by the aluminum chelate compound of the present invention was examined.

Namely, the aluminum compound was added in an amount of 5% by weight to a commercially available ink, and the mixture was kneaded and the color-developing test was carried out.

From the naked eye comparison with the blank free of the aluminum compound, it was found that the sharpness was apparently improved by the aluminum compound of the present invention.

This effect results in a definite difference of the reflectance on the surface of a test piece for the color-developing test. More specifically, when the tristimulus values X, Y and Z were measured by a color difference meter, it was found that the values corresponding to complementary colors of the respective inks were reduced. Namely, in case of the red ink, the value Z was reduced, in case of the blue ink, the value X was reduced, and in case of the black ink, the values X, Y and Z were reduced. Reduction ratios of the values X, Y and Z to those of the blank ink free of the aluminum compound are shown in Table 1.

TABLE 1

| Aluminum Compound | Reduction Ratio (%) | | |
| --- | --- | --- | --- |
| | X | Y | Z |
| (1) | 18 | 19 | 18 |
| (8) | 8 | 12 | 5 |
| (9) | 6 | 10 | −3 |
| (10) | 4 | 10 | −1 |
| (11) | 7 | 7 | 2 |
| (16) | 17 | 16 | 11 |
| (17) | 23 | 23 | 23 |
| (19) | 21 | 21 | 21 |

EXAMPLE 2

The effect of improving the dispersibility by the aluminum chelate compound of the present invention was examined.

Namely, 0.03 g of the aluminum chelate compound of the present invention, 0.3 g of titanium dioxide and 30 ml of xylene were charged in a test tube, and the test tube was shaken to disperse titanium dioxide in xylene. The degree of sedimentation of titanium dioxide was determined after the dispersion had been allowed to stand still for a certain time, and the relation between the standing time and the degree of sedimentation was compared with the same relations observed in the comparative and blank samples.

Comparative samples used:
Comparison (1): commercially available dispersant (diamine oleate).
Comparison (2): blank.

Degree of sedimentation: (height of sedimented titanium dioxide/height of solution)×100.

The obtained results are shown in Table 2.

TABLE 2

| Aluminum Compound | Standing Time (hours) | | | | | |
| --- | --- | --- | --- | --- | --- | --- |
| | 0 | 6 | 24 | 48 | 72 | 120 |
| (1) | 100 | 98 | 91 | 80 | 67 | 50 |
| (2) | 100 | 98 | 90 | 80 | 60 | 40 |
| (3) | 100 | 98 | 90 | 78 | 57 | 31 |
| (4) | 100 | 98 | 90 | 80 | 67 | 40 |
| (5) | 100 | 98 | 92 | 83 | 73 | 56 |
| (8) | 100 | 98 | 90 | 70 | 60 | 30 |
| (11) | 100 | 98 | 88 | 65 | 46 | 25 |
| (15) | 100 | 98 | 85 | 72 | 58 | 37 |
| (16) | 100 | 98 | 86 | 74 | 64 | 43 |
| (18) | 100 | 98 | 85 | 73 | 62 | 41 |
| (20) | 100 | 98 | 84 | 69 | 57 | 36 |
| (21) | 100 | 98 | 85 | 73 | 63 | 43 |
| Comparison (1) | 100 | 100 | 50 | 2 | 2 | 2 |
| Comparison (2) | 100 | 100 | 2 | 2 | 2 | 2 |

EXAMPLE 3

The effect of reducing the viscosity of a dispersion of the filler or the like by the aluminum compound of the present invention was examined.

More specifically, the compound (1) was mixed with calcium carbonate at a ratio shown in Table 3, and the mixture was sufficiently kneaded in a mortar to effect the surface treatment of calcium carbonate. The so-treated calcium carbonate was added to liquid paraffin and the viscosity was measured at 25° C. by a B-type rotational viscometer. The obtained results are shown in Table 3.

TABLE 3

| Ingredients (parts by weight) | Composition No. | | | | | |
|---|---|---|---|---|---|---|
| | 1 | 2 | 3 | 4 | 5 | 6 |
| Calcium carbonate | 50 | 50 | 67 | 67 | 67 | 67 |
| Liquid paraffin | 50 | 50 | 33 | 33 | 33 | 33 |
| Compound (1) | 0 | 0.5 | 0 | 0.5 | 1.0 | 2.0 |
| Viscosity (cP, 25° C.) | measurement impossible | 330 | above 100,000 | 2,200 | 1,100 | 980 |

EXAMPLE 4

The test was carried out in the same manner as described in Example 3 by using the aluminum compound (1), dioctyl phthalate (DOP) and calcium carbonate, and the viscosity was measured at 25° C. The obtained results are shown in Table 4.

TABLE 4

| Ingredients (parts by weight) | Composition No. | | | |
|---|---|---|---|---|
| | 1 | 2 | 3 | 4 |
| Calcium carbonate | 50 | 50 | 67 | 67 |
| DOP | 50 | 50 | 33 | 33 |
| Compound (1) | 0 | 0.5 | 0 | 1.0 |
| Viscosity (cP, 25° C.) | measurement impossible | 270 | above 100,000 | 1,940 |

EXAMPLE 5

The test was carried out in the same manner as described in Example 3 by using the aluminum compound (1), liquid paraffin and titanium dioxide, and the viscosity was measured at 25° C. The obtained results are shown in Table 5.

TABLE 5

| Ingredients (parts by weight) | Composition | | |
|---|---|---|---|
| | 1 | 2 | 3 |
| Titanium dioxide | 50 | 50 | 50 |
| Liquid paraffin | 50 | 50 | 50 |
| Compound (1) | 0 | 1.0 | 2.0 |
| Viscosity (cP, 25° C.) | above 100,000 | 6,070 | 1,430 |

EXAMPLE 6

The test was carried out in the same manner as described in Example 3 by using the aluminum compound (1), liquid paraffin and aluminum hydroxide, and the viscosity was measured at 25° C. The obtained results are shown in Table 6.

TABLE 6

| Ingredients (parts by weight) | Composition No. | |
|---|---|---|
| | 1 | 2 |
| Aluminum hydroxide | 67 | 67 |
| Liquid paraffin | 33 | 33 |
| Compound (1) | 0 | 0.5 |
| Viscosity (cP, 25° C.) | 31,000 | 1,910 |

EXAMPLE 7

The viscosity-reducing effects by various aluminum compounds of the present invention were examined.

More specifically, 0.2 g of the aluminum compound of the present invention, 10 g of calcium carbonate and 10 g of liquid paraffin were sufficiently mixed in a mortar, and the viscosity was measured at 25° C. in the same manner as described in Example 3. The obtained results are shown in Table 7.

TABLE 7

| Aluminum Compound No. | Viscosity (cP, 25° C.) |
|---|---|
| (2) | 65 |
| (8) | 68 |
| (9) | 83 |
| (10) | 85 |
| (12) | 84 |
| (14) | 63 |
| (15) | 82 |
| (16) | 68 |
| (17) | 87 |
| (18) | 70 |
| (19) | 69 |
| Blank | measurement impossible because of too high viscosity |

EXAMPLE 8

In a Henschel mixer, 100 parts by weight of calcium carbonate having an average particle size of 2μ was treated with 3 parts by weight of the aluminum chelate compound of the present invention, and then, the treated calcium carbonate was added to 100 parts by weight of a granular polypropylene resin and the mixture was kneaded and pulverized for 10 minutes by a two-roll mixer maintained at 177° C. The resulting pulverized composition was injection-molded into a plate at 200° C. under 5.1 kg/cm² for a mold-seal time of 30 seconds. The notched Izod impact strength value of the molded plate was measured. The obtained results are shown in Table 8.

TABLE 8

| Aluminum Compound No. | Notched Izod Impact Strength (kg · cm/cm) |
|---|---|
| (1) | 4.5 |
| (10) | 4.7 |
| (11) | 4.2 |
| (15) | 4.2 |
| (17) | 4.0 |
| Blank | 3.0 |

I claim:

1. A surface modifier for a powdery or granular substance having a hydrophilic surface, which comprises at least one aluminum chelate compound represented by the following general formula (I) or (II):

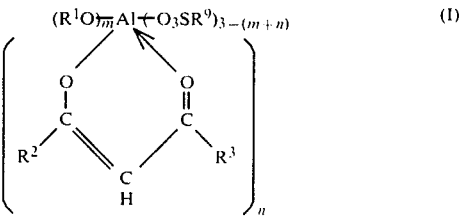

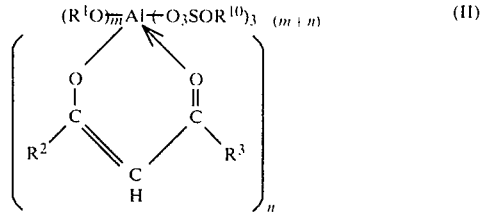

wherein $R^1$ is at least one member selected from the group consisting of a hydrogen atom and an alkyl group having 1 to 6 carbon atoms, $R^2$ is at least one member selected from the group consisting of methyl and phenyl groups, $R^3$ is at least one member selected from the group consisting of $R^4$—, $R^5O$— and $R^6NH$— (wherein $R^4$, $R^5$ and $R^6$ independently represent an alkyl group having 1 to 22 carbon atoms or an alkenyl, aryl, aralkyl or alkylaryl group having 3 to 22 carbon atoms), $R^9$ and $R^{10}$ independently represent an alkyl group having 1 to 22 carbon atoms or an alkenyl, aryl, aralkyl or alkylaryl group having 3 to 22 carbon atoms, $R^3$ may be the same as or different from $R^9$ and $R^{10}$, with the proviso that at least one of $R^3$, $R^9$ and $R^{10}$ is a substituent having at least 8 carbon atoms or a polymerizable alkenyl group, and m and n are mean values per molecule which satisfy the requirements of m=0.5 to 2.7, n=0.3 to 2.5 and m+n=0.8 to 3.

2. A surface modifier for a powdery of granular substance having a hydrophilic surface, which comprises at least one aluminum chelate compound represented by the following general formula (III), (IV) or (V):

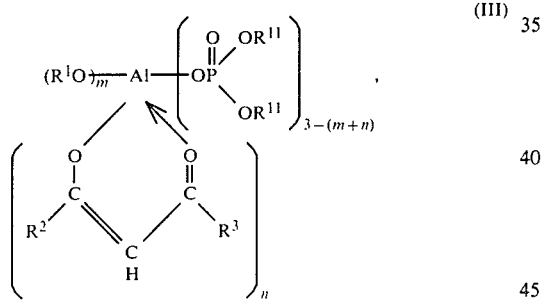
(III)

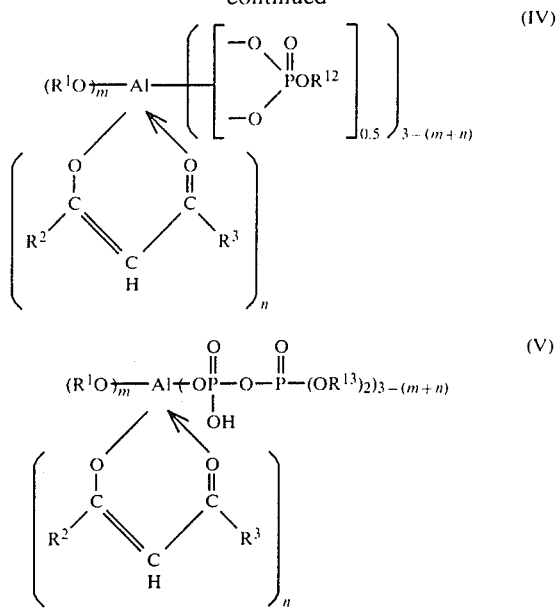

wherein $R^1$ is at least one member selected from the group consisting of a hydrogen atom and an alkyl group having 1 to 6 carbon atoms, $R^2$ is at least one member selected from the group consisting of methyl and phenyl groups, $R^3$ is at least one member selected from the group consisting of $R^4$—, $R^5O$— and $R^6NH$— (wherein $R^4$, $R^5$ and $R^6$ independently represent an alkyl group having 1 to 22 carbon atoms or an alkenyl, aryl, aralkyl or alkylaryl group having 3 to 22 carbon atoms), $R^{11}$, $R^{12}$ and $R^{13}$ independently represent an alkyl group having 1 to 22 carbon atoms or an alkenyl, aryl, aralkyl or alkylaryl group having 3 to 22 carbon atoms, $R^3$ may be the same as or different from $R^{11}$, $R^{12}$ and $R^{13}$, with the proviso that at least one of $R^3$, $R^{11}$, $R^{12}$ and $R^{13}$ is a substituent having at least 8 carbon atoms or a polymerizable alkenyl group, and m and n are mean values per molecule which satisfy the requirements of m=0.5 to 2.7, n=0.3 to 2.5 and m+n=0.8 to 3.

* * * * *